(12) United States Patent
Surritte et al.

(10) Patent No.: US 8,497,412 B2
(45) Date of Patent: Jul. 30, 2013

(54) LOBLOLLY PINE TREE NAMED '96GE0034'

(75) Inventors: George Surritte, Summerville, SC (US);
Jeffery Alan Wright, Mt Pleasant, SC (US); Mark Rutter, Goose Creek, SC (US)

(73) Assignee: Arborgen, LLC, Ridgeville, SC (US)

( * ) Notice: Subject to any disclaimer, the term of this patent is extended or adjusted under 35 U.S.C. 154(b) by 493 days.

(21) Appl. No.: 12/584,003

(22) Filed: Aug. 28, 2009

(65) Prior Publication Data

US 2010/0058491 A1   Mar. 4, 2010

Related U.S. Application Data

(60) Provisional application No. 61/093,074, filed on Aug. 29, 2008.

(51) Int. Cl.
*A01H 7/00* (2006.01)
*A01H 4/00* (2006.01)
*A01H 1/00* (2006.01)
*C12N 15/82* (2006.01)

(52) U.S. Cl.
USPC ............ 800/319; 800/260; 800/268; 435/410

(58) Field of Classification Search
None
See application file for complete search history.

(56) References Cited

U.S. PATENT DOCUMENTS 6,372,494 B1   4/2002   Naughton et al.
2007/0079408 P1 *   4/2007   Pait et al.

OTHER PUBLICATIONS

Devey et al (Theor Appl Genet 83: 238-242, 1991).*
McKeand et al (Silvae Genetica 47(4): 223-234, 1998).*
Bramlett (Journal of Forestry 95(3): 15-19, 1997).*
Auckland et al., *Conifer Microsatellite Handbook*, Texas A&M University, College Station, TX 2002.
Becwar and Pullman, Somatic Embryogenesis in Loblolly Pine (*Pinus taeda* L.), *IPST Technical Paper Series No. 528*, Institute of Paper Science and Technology, Jul. 1994, pp. 1-18.
Bramlett, D.L., "Genetic Gain from Mass Controlled Population and Topworking," *Journal of Forestry*, Mar. 1997, vol. 95, No. 3, pp. 15-19.
Dorman, K.W., *The Genetics and Breeding of Southern Pins*, USDA Agricultural Handbook No. 471, Jul. 1976, pp. 24-51.
Doyle and Doyle, "A Rapid DNA Isolation Procedure for Small Quantities of Fresh Leaf Tissue," *Phytochem. Bull.*, 1987, vol. 19, pp. 11-15.
Duryea and Dougherty, *Forest Regeneration Manual*, Kluwer Academic Publishers, 1991, p. 433.
Echt et al., "An Integrated and Annotated Microsatellite Map of Loblolly Pine," IUFRO-CITIA Joint Meeting. Adaptation, Breeding and Conservation in the Era of Forest Tree Genomics and Environmenal Change. Quebec City, Canada, Aug. 25-28, 2008.
Liewlaksaneeyanawin et al., "Single-copy, Species-transferable Microsatellite Markers Developed from Loblolly Pine ESTs," *Theor. Appl. Genetics*, 2004, vol. 109, No. 2, pp. 361-369.
Nelson et al., "Loblolly Pine SSR Markers for Shortleaf Pine Genetics," Shortleaf Pine Restoration and Ecology in the Ozarks: Proceedings of a Symposium: Nov. 7-9, 2006, Springfield, MO., Gen. Tech. Rep. NRS-P-15, USDA Forest Service, Northern Research Station, 2007, pp. 95-98.
Pullman and Johnson, "Somatic Embryogenesis in Loblolly Pine (*Pinus taeda* L.) Improving Culture Initiation Rates,",*Ann. For. Sci.*, 2002, vol. 50, pp. 663-668.
*Seeds of Woody Plants in the United States*, USDA Agricultural Handbook No. 450, 1974, pp. 608-631.
Tautz, D., "Hypervariability of Simple Sequences as a General Source of Polymorphic DNA Markers," *Nucleic Acids Res.*, 1989, vol. 17, No. 16, pp. 6463-6471.
Echt et al., "An Integrated and Annotated Microsatellite Map of Loblolly Pine," IUFRO-CITIA Joint Meeting. Adaptation, Breeding and Conservation in the Era of Forest Tree Genomics and Environmental Change. Quebec City, Canada, Aug. 25-28, 2008. (Abstract) 2 pages.

* cited by examiner

*Primary Examiner* — Shubo (Joe) Zhou
*Assistant Examiner* — Keith Robinson
(74) *Attorney, Agent, or Firm* — Foley & Lardner LLP (57) ABSTRACT

A new and distinct variety of loblolly pine tree named '96GE0034', particularly characterized by excellent stem straightness, high biomass production, uniform rapid growth and good fusiform rust resistance.

13 Claims, 2 Drawing Sheets
(2 of 2 Drawing Sheet(s) Filed in Color)

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<223> OTHER INFORMATION: Universal m13-F sequence

<400> SEQUENCE: 1
cacgacgttg taaaacgac                                              19

<210> SEQ ID NO 2
<211> LENGTH: 41
<212> TYPE: DNA
<213> ORGANISM: Pinus taeda
<220> FEATURE:
<221> NAME/KEY: misc_feature
<223> OTHER INFORMATION: PtRIP_0619 Primer

<400> SEQUENCE: 2
cagctctctt aatagcctcg ggcacatagc aacgctgaag a                41

<210> SEQ ID NO 3
<211> LENGTH: 40
<212> TYPE: DNA
<213> ORGANISM: Pinus taeda
<220> FEATURE:
<221> NAME/KEY: misc_feature
<223> OTHER INFORMATION: PtRIP_1040 Primer

<400> SEQUENCE: 3
tcaaggaatt cattggagcc tttggccata tcaaacccat                  40

<210> SEQ ID NO 4
<211> LENGTH: 41
<212> TYPE: DNA
<213> ORGANISM: Pinus taeda
<220> FEATURE:
<221> NAME/KEY: misc_feature
<223> OTHER INFORMATION: PtRIP_1077 Primer

<400> SEQUENCE: 4
aacattctag catgccccac ttgtggtgga tgtctctcct c                41

<210> SEQ ID NO 5
<211> LENGTH: 40
<212> TYPE: DNA
<213> ORGANISM: Pinus taeda
<220> FEATURE:
<221> NAME/KEY: misc_feature
<223> OTHER INFORMATION: PtSIFG_0193 Primer

<400> SEQUENCE: 5
cccatgcatc aattcaagtt tgtgcgtgga tatggaaaaa                  40

<210> SEQ ID NO 6
<211> LENGTH: 40
<212> TYPE: DNA
<213> ORGANISM: Pinus taeda
<220> FEATURE:
<221> NAME/KEY: misc_feature
<223> OTHER INFORMATION: PtSIFG_0493 Primer

<400> SEQUENCE: 6
gagaacatct gccttgagcc ctggcatgat gggtttctct                  40

<210> SEQ ID NO 7
<211> LENGTH: 40
<212> TYPE: DNA
<213> ORGANISM: Pinus taeda
<220> FEATURE:
<221> NAME/KEY: misc_feature
<223> OTHER INFORMATION: PtSIFG_0566 Primer

<400> SEQUENCE: 7
acttagtggg aaggggggaa ttcctcagcc aaaagctctc                  40

<210> SEQ ID NO 8
<211> LENGTH: 40
<212> TYPE: DNA
<213> ORGANISM: Pinus taeda
<220> FEATURE:

```
<221> NAME/KEY: misc_feature
<223> OTHER INFORMATION: PtSIFG_0737 Primer

<400> SEQUENCE: 8
gcaaggggaa ttgcttatga gggatcgcat cagctgtaat                                40

<210> SEQ ID NO 9
<211> LENGTH: 40
<212> TYPE: DNA
<213> ORGANISM: Pinus taeda
<220> FEATURE:
<221> NAME/KEY: misc_feature
<223> OTHER INFORMATION: PtSIFG_1190 Primer

<400> SEQUENCE: 9
caggtggctt ggatttcatt tcattcaagc gtcctgctta                                40

<210> SEQ ID NO 10
<211> LENGTH: 40
<212> TYPE: DNA
<213> ORGANISM: Pinus taeda
<220> FEATURE:
<221> NAME/KEY: misc_feature
<223> OTHER INFORMATION: PtSIFG_4222 Primer

<400> SEQUENCE: 10 caccctttc acgcaagaat gcctacgcat tatccttcca                                 40

<210> SEQ ID NO 11
<211> LENGTH: 40
<212> TYPE: DNA
<213> ORGANISM: Pinus taeda
<220> FEATURE:
<221> NAME/KEY: misc_feature
<223> OTHER INFORMATION: PtSIFG_4223 Primer

<400> SEQUENCE: 11
agggaaaccg cggattatag ccggaatgaa gattgcagtt                                40

<210> SEQ ID NO 12
<211> LENGTH: 39
<212> TYPE: DNA
<213> ORGANISM: Pinus taeda
<220> FEATURE:
<221> NAME/KEY: misc_feature
<223> OTHER INFORMATION: PtSIFG_4304 Primer

<400> SEQUENCE: 12
catgcatgtg tggaggagtc tcatgtgctt tgatccct                                  39

<210> SEQ ID NO 13
<211> LENGTH: 42
<212> TYPE: DNA
<213> ORGANISM: Pinus taeda
<220> FEATURE:
<221> NAME/KEY: misc_feature
<223> OTHER INFORMATION: PtTX_4114 Primer

<400> SEQUENCE: 13
acacatgtct tgaggagttc aatttgatct ataactttca cc                             42

<210> SEQ ID NO 14
<211> LENGTH: 39
<212> TYPE: DNA
<213> ORGANISM: Pinus taeda
<220> FEATURE:
```

```
<221> NAME/KEY: misc_feature
<223> OTHER INFORMATION: SsrPt_ctg9249 Primer

<400> SEQUENCE: 14
ctgctccctc agctcttcca gacgtcactg ccattaccc                                          39
```

LOBLOLLY PINE TREE NAMED '96GE0034'

CROSS-REFERENCE TO RELATED PATENT APPLICATIONS

This application claims priority from U.S. Provisional Application No. 61/093,074, filed Aug. 29, 2008, incorporated herein by reference in its entirety.

FIELD OF THE INVENTION

The present invention relates to a new, distinct and stable variety of pine tree, botanically known as *Pinus taeda* L. of the Pinaceae family, commonly known as loblolly pine, and hereinafter referred to by the variety denomination '96GE0034'. The present invention relates to tissue cultures which are the loblolly pine '96GE0034', as well as, plants and plant parts, such as, pollen, seeds, cones, inflorescence, needles, embryos, cuttings, seedlings, bark, wood, oils, lumber or timber obtained from plants having all of the morphological and physiological characteristics of loblolly pine '96GE0034'. The present invention further relates to harvested products obtained from loblolly pine '96GE0034', such as wood, pulp or paper. The present invention also relates to methods for producing '96GE0034' tissue cultures, regenerating '96GE0034' plants therefrom, as well as progeny of the loblolly pine '96GE0034'. The present invention relates to a method of producing loblolly pine wherein the method is somatic embryogenesis comprising the tissue culture and regeneration of the loblolly pine '96GE0034' plants. The invention further relates to making root cuttings of the reproduced '96GE0034' plants and planting the root cuttings. The present invention also relates to a method of producing loblolly pine progeny or hybrids thereof, comprising the steps of (a) crossing loblolly pine '96GE0034', either as the female or seed parent or male or pollen parent, with a second pine variety, and (b) selecting progeny. The present invention also relates to a method of producing loblolly pine progeny or hybrids thereof, comprising the steps of (a) crossing loblolly pine '96GE0034', as either the female or seed parent or male or pollen parent, with a second pine variety, (b) harvesting seeds produced from said cross, and (c) producing and selecting progeny from said harvested seeds. Furthermore, the present invention relates to a method of producing loblolly pine progeny, comprising the steps of selfing loblolly pine '96GE0034', and (b) selecting progeny.

BACKGROUND OF THE INVENTION

The present invention relates to a new, distinct and stable variety of pine tree, botanically known as *Pinus taeda* of the Pinaceae family, commonly known as a loblolly pine, also known as Arkansas pine, North Carolina pine and oldfield pine, and hereinafter referred to by the variety denomination '96GE0034'.

Loblolly pine is native to the southeastern United States. Typical loblolly pine grows within a range of about 30 to 35 m in height and about 0.4 to 1.5 m in diameter. Needles of loblolly pine are arranged in bundles of three, which are sometimes twisted, and measure within a range of about 12 to 22 cm. Cones of loblolly pine are initially green in color, maturing to a pale brown, measure within a range of i) about 7 to 13 cm in length, and ii) about 2 to 3 cm in width when closed, and maturing to about 4 to 6 cm in width once opened, and contain scales with a sharp spine about 3 to 6 mm in length.

Loblolly pine has a vigorous growth rate and is grown for lumber and pulp fibers. Methods for reproduction and cultivation of loblolly pine are well known. For a detailed discussion, reference is made to the following publications, which are incorporated by reference: Becwar and Pullman, *IPST Technical Paper Series No.* 528, Institute of Paper Science and Technology, 1994, pp. 1-18; Pullman and Johnson, *Ann. For. Sci.*, Vol. 50, 2002, pp. 663-668; *Seeds of Woody Plants in the United States*, USDA Agricultural Handbook, No. 450, 1974, pp. 608-631; Dorman, K. W., *The Genetics and Breeding of Southern Pines*, USDA Agricultural Handbook 471, 1976, pp. 24-51; Duryea and Dougherty, *Forest Regeneration Manual*, Kluwer Academic Publishers, 1991, p. 433.

Since loblolly pine is a commercially important forest species, research studies have been undertaken to identify promising loblolly pine varieties and hybrids which express a) resistance to problematic diseases and pests, such as fusiform rust and bark beetles, b) weather tolerance, such as extreme cold and drought tolerance c) stem strength and straightness, d) improved wood quality, and e) vigorous growth rate. Research studies have been conducted to identify such promising loblolly pine varieties and hybrids. In addition, the distinctive genetic fingerprint for these varieties can be analyzed. Numerous reproductive methods have been developed for loblolly pine varieties. In particular, asexual propagation by somatic embryogenesis is described in U.S. Pat. No. 6,372,494 for conifers, and in U.S. Patent Application Publication No. 2007-0079408-P1 for loblolly pine.

SUMMARY OF THE INVENTION

The present invention provides a new loblolly pine tree selection that possesses excellent stem straightness, high biomass production, uniform rapid growth and good fusiform rust resistance.

These and other objectives have been achieved in accordance with the present invention which provides '96GE0034' as a new, distinct and stable variety of loblolly pine that is a product of a planned breeding program conducted by the inventors in 1995 in Ravenel, S.C. The new loblolly pine '96GE0034' is a progeny of a first-generation selection pollinated by a first-generation selection. The female or seed parent is the unpatented *Pinus taeda* variety designated 7-56 selected in Williamsburg County, South Carolina, and is a first-generation selection. The male or pollen parent is the unpatented *Pinus taeda* variety designated 9-6 selected in Brunswick County, North Carolina, and is a first-generation selection.

Tissue culture of the new loblolly pine '96GE0034' is deposited with the American Culture Type Collection (ATCC), 10801 University Boulevard, Manassas, Va. 20110-2209. 25 frozen, callus tissue cultures of loblolly pine '96GE0034' were deposited with the ATCC on Jul. 10, 2008, and accorded ATCC Patent Deposit Designation No.: PTA-9358. For the purpose of this application, the designation GE34 is equivalent to '96GE0034', the designation used by the ATCC in handling this deposit. Because any plant produced from the tissue culture of the new loblolly pine '96GE0034' is a clone, the unique characteristics of '96GE0034' are implemented at every planting spot in a stand. This leads to stands with high uniformity in growth and quality.

OBJECTS OF THE INVENTION

The present invention relates to tissue cultures which produce the loblolly pine '96GE0034'. The present invention also relates to loblolly pine, and plant parts thereof, that is loblolly pine '96GE0034'. The present invention also relates to loblolly pine, and plant parts thereof, having all of the morphological and physiological characteristics of loblolly pine '96GE0034'. The present invention also relates to plant parts, such as pollen, seeds, cones, inflorescence, needles, embryos, cuttings, seedlings, bark, wood, oils, lumber or timber produced by loblolly pine '96GE0034'. The present invention also relates to harvested products or extractives of loblolly pine '96GE0034', such as wood, pulp, oil, or paper.

The present invention relates to a method of producing a loblolly pine variety, wherein the method is somatic embryogenesis comprising the tissue culture of the loblolly pine '96GE0034'. This method may further comprise making root cuttings from the reproduced '96GE0034' and planting the root cuttings.

The present invention also relates to a method of producing loblolly pine progeny or hybrid thereof, comprising the steps of (a) crossing loblolly pine '96GE0034', either as the female or seed parent or male or pollen parent, with a second pine variety, and (b) selecting progeny. The second pine variety may also be '96GE0034'. In addition, this method may further comprise making progeny of '96GE0034' through wind pollination, controlled pollination, or mass controlled pollination.

The present invention also relates to a method of producing loblolly pine progeny or hybrids thereof, comprising the steps of (a) crossing loblolly pine '96GE0034', as either the female or seed parent or male or pollen parent, with a second pine variety, (b) harvesting seeds produced from said cross, and (c) producing and selecting progeny from said harvested seeds. The second pine variety may also be '96GE0034'.

The present invention also relates to a method of producing loblolly pine progeny, comprising the steps of selfing loblolly pine '96GE0034', and (b) selecting progeny.

BRIEF DESCRIPTION OF THE PHOTOGRAPHS

The patent or application file contains drawings executed in color. Copies of this patent or patent application publication with color drawings will be provided by the Office upon request and payment of the necessary fees.

The accompanying photographs illustrate the overall appearance of the new loblolly pine tree '96GE0034' showing the colors as true as is reasonably possible with colored reproductions of this type. Colors in the photographs may differ slightly from the color values cited in the detailed botanical description, which accurately describe the color of '96GE0034'.

DETAILED DESCRIPTION OF THE INVENTION

The present invention provides '96GE0034' as a new, distinct and stable variety of loblolly pine that is a product of a planned breeding program conducted by the inventors in 1995 in Ravenel, S.C. The objective of the planned breeding program was to develop a new loblolly pine tree with vigorous growth, high biomass production for fiber or fuel use, straight stem and high resistance to fusiform rust infection that would achieve commercial maturity sooner than typical loblolly pine trees in the Southeast coastal zone of the United States.

For the purposes of this application, the term "variety" is equivalent to a clone, as '96GE0034' may be reproduced asexually and all of the clones are essentially identical genetically.

For the purposes of this application, during "mass control pollination" (MCP) a large number of female strobili are pollinated and produce seedlings (or rooted cuttings) for use in regeneration. The large scale of MCP distinguishes this process from traditional "controlled pollination" (CP), which is used to produce seed for progeny tests in order to evaluate the genetic value of the parents. Bramlett, D L. 1997. Genetic Gain from Mass Controlled Pollination and Topworking. Journal of Forestry, vol. 95, p 15-19. Another difference between MCP and CP is the amount of control that is used to reduce contamination. CP flowers are isolated from any outside pollen contamination and pollen is collected and processed to be nearly 100% free of contaminating pollen. In CP, the goal is that every seed has a known mother and father. The MCP process allows some contamination, so faster and less expensive techniques are used to produce large quantities of seed with the majority of the seed having a known mother and a known father.

The following traits have been repeatedly observed and are determined to be unique characteristics of '96GE0034' which in combination distinguish this loblolly pine tree as a new and distinct loblolly pine variety:
 1. Excellent stem straightness;
 2. High biomass production;
 3. Uniform, rapid growth;
 4. Good fusiform rust resistance.

In comparison to the full-sibling family of which it is a member, '96GE0034' differs primarily in the traits listed in Table 1.

TABLE 1

| Trait | New Variety '96GE0034' | Family 7-56 × 9-6 |
| --- | --- | --- |
| Straightness | Very good | Moderate to good |
| Growth | Rapid | Low to high |
| Rust infection | Low | Low to high |
| Forking | Low | Low to high |
| Branch angle | Moderate | Moderate to steep |
| Branch allocation | High | Moderate to high |

Of the many commercial varieties known to the present inventors, the most similar in comparison to the new loblolly pine '96GE0034' is *Pinus* designated AA32 (unpatented), and '96GE0034' differs from AA32 primarily in the traits listed in Table 2:

TABLE 2

| Trait | New Variety '96GE0034' |
| --- | --- |
| Straightness | Superior to AA32 |
| Growth | Superior to AA32 |
| Stand uniformity | Greater uniformity than AA32 |
| Rust resistance | High for GE34 and very high for AA32 |
| Branch allocation | Greater than AA32 |
| Forking | Less than AA32 |

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

EXAMPLES

Example 1

Breeding of '96GE0034'

The new *Pinus* variety is a product of a controlled breeding program conducted by the inventors, in Ravenel, S.C. The objective of the breeding program was to develop a new loblolly pine tree with vigorous growth, straight stem and high resistance to fusiform rust infection that would achieve commercial maturity sooner than typical trees in the Southeast coastal zone.

The new *Pinus* variety originated from a cross made by the inventors in 1995 in Ravenel, S.C. The new *Pinus* variety is a progeny of a first-generation selection pollinated by a first-generation selection. The female or seed parent is the unpatented *Pinus taeda* variety designated 7-56 selected in Williamsburg County, South Carolina, and is a first-generation selection. The male or pollen parent is the unpatented *Pinus taeda* variety designated 9-6 selected in Brunswick County, North Carolina, and is a first-generation selection.

Cross pollination occurred in 1995 followed by induction of somatic embryogenesis tissue and cyropreservation of embryogenic tissue in 1996 in Summerville, S.C. The first somatic seedlings of the new *Pinus* variety were produced in 1998 and then planted in October, 1998, in 2 field experiments located in Berkeley and Allendale Counties, South Carolina. Among these 2 field experiments, a total of 20 ramets of the new *Pinus* variety were planted (10 ramets per field experiment). Additional ramets of the new *Pinus* variety were produced and planted in 2 field experiments in October, 1999, in Berkeley and Allendale Counties, South Carolina (each contained 10 ramets).

The new *Pinus* variety was discovered and selected by the inventors within the progeny of the stated cross in 2004. The new *Pinus* variety was selected by the inventors based on stem straightness, rapid growth and fusiform rust resistance.

Asexual reproduction of the new *Pinus* variety by somatic embryogenesis, a tissue culture technique for embryo multiplication, was first performed in August, 1996, in Summerville, S.C., and the propagated variety has demonstrated that the combination of characteristics as herein disclosed for the new variety are firmly fixed and retained through successive generations of asexual reproduction. The new variety reproduces true to type.

Example 2

Description of '96GE0034'

The new *Pinus* '96GE0034' has not been observed under all possible environmental conditions. The phenotype of the new loblolly pine tree variety may vary with environmental variations such as temperature, light intensity and day length, as well as, growing conditions variations such as irrigation, fertilization, pruning, and pest control, without any change in the genotype of the new loblolly pine tree variety.

Figure 1:
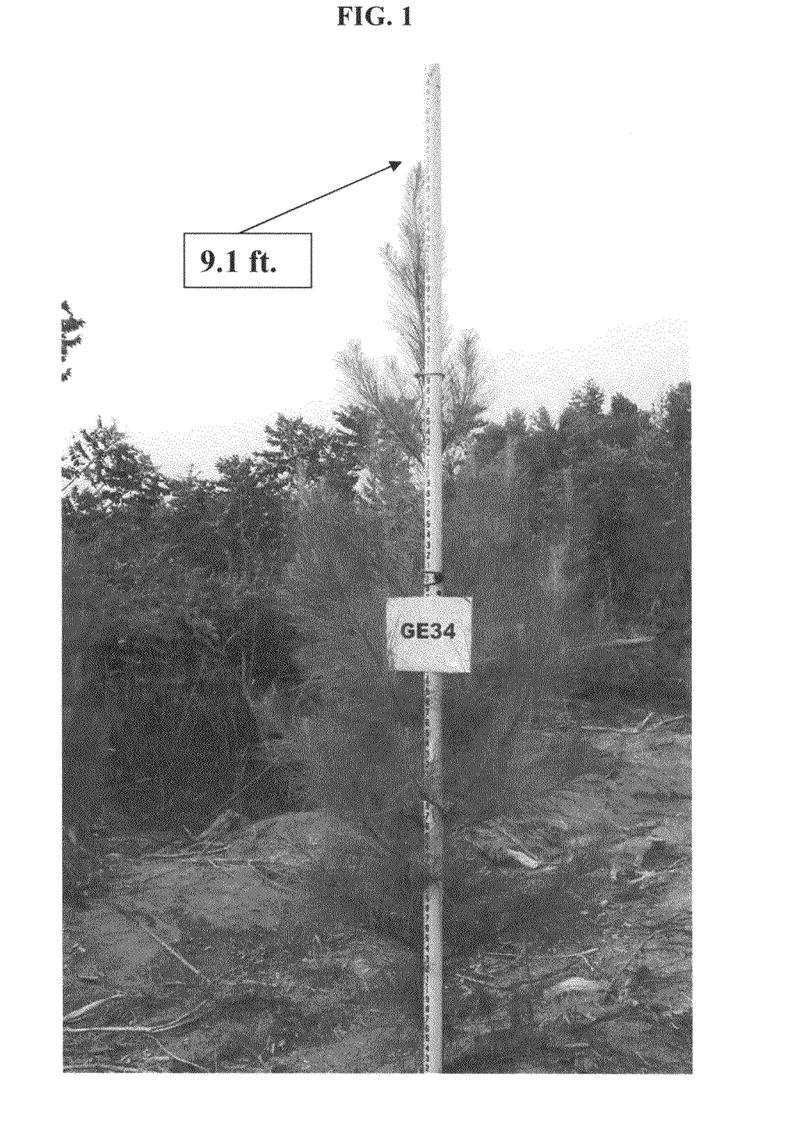
FIG. 1 shows a side perspective view of a loblolly pine tree of '96GE0034', at age 2, grown in a field experiment in Berkeley County, South Carolina, which shows the stem straightness of '96GE0034'.
Figure 2:
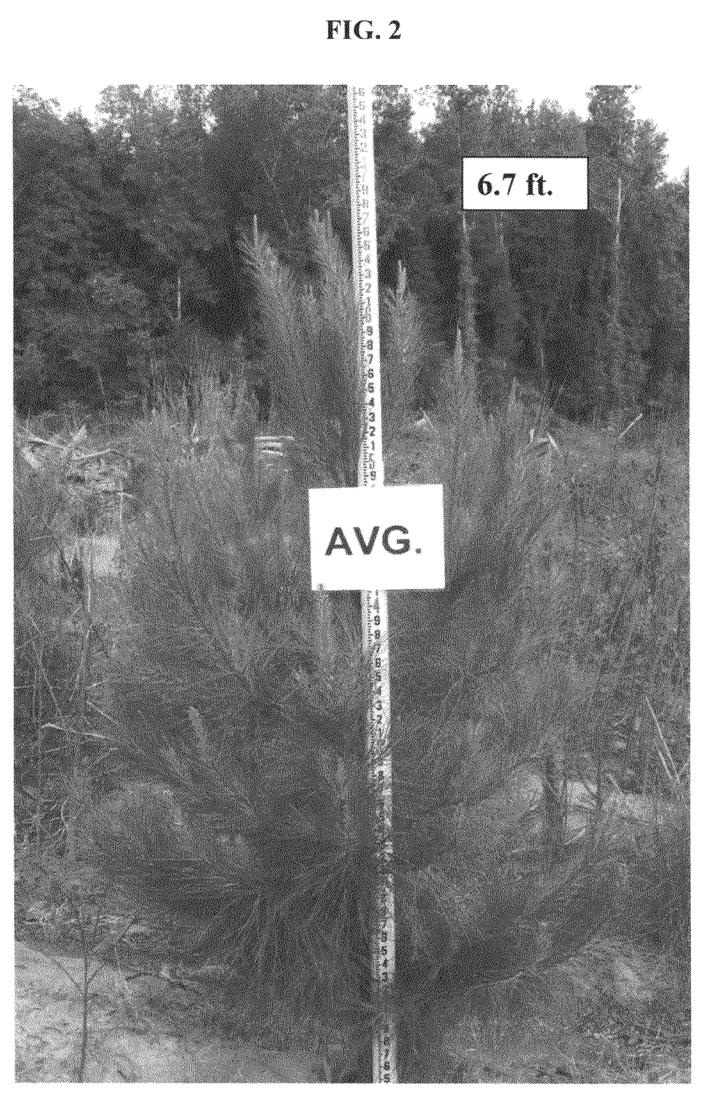
FIG. 2 shows a side perspective view of a loblolly pine tree variety with average growth performance, at age 2, grown in a field experiment in Berkeley County, South Carolina.

The aforementioned photographs, together with the following observations, measurements and values describe loblolly pine trees of '96GE0034' as grown in the pine farm in Berkeley County, South Carolina, under conditions which closely approximate those generally used in commercial practice.

Unless otherwise stated, the detailed botanical description includes observations, measurements and values based on 4-year old '96GE0034' trees grown in the pine farm in Berkeley County, South Carolina, from 1999 to 2003. Quantified measurements are expressed as an average of measurements taken from a number of trees of '96GE0034'. The measurements of any individual tree, or any group of trees, of the new variety may vary from the stated average.

Color references are made to the Munsell Color Charts For Plant Tissues (MCC), 1968 edition, except where general colors of ordinary significance are used. Color values were taken under daylight conditions at approximately 1 a.m. EST in Berkeley County, South Carolina.

All of the trees of '96GE0034', insofar as they have been observed, have been similar in all the characteristics described below.

Classification:
Botanical: *Pinus taeda*
Parentage:
Female or Seed Parent: *Pinus taeda* variety designated '7-56' (unpatented), selected in Williamsburg County, South Carolina, and is a first-generation selection.
Male or Pollen Parent: *Pinus taeda* variety designated '9-6' (unpatented), selected in Brunswick County, North Carolina, and is a first-generation selection.
Propagation: Somatic Embryogenesis
Growing Conditions:
Light intensities: Full sunlight.
Temperature: Average summer maximum temperature of 90 degrees F., and average minimum winter temperature of 36 degrees F.
Fertilization: None.
Growth regulators: None.
Pruning or trimming requirements: None.
Tree:
Age: Observed trees were 4 years old.
Vigor: The height growth rate of '96GE0034' is $6^{th}$ among 90 loblolly pine varieties, at about 180 cm of terminal growth per year.
Form and Habit: A pine tree that is upright and conical in shape with whorled, larger diameter branches that form moderate angle to the trunk. Canopy is broader than typical loblolly pine trees. The occurrence of rust infections is low. We expect a mature tree of '96GE0034' to approach 33 m in height at age 25.
Branching habit: Whorled. Main branches angle is 35° to 45° with respect to trunk if allowed to grow naturally.
Size (4 Years Old):
Height: About 7 m
Spread: About 4 m
Roots:
Time to initiate roots: About 4 to 6 weeks.
Trunk:
Height: About 1 m to 1.5 m to lowest live limb.
Diameter: About 12.2 cm
Texture: Bark texture varies by age. Immature bark is scaly and mature bark is irregularly blocky.
Bark color: Primarily MCC 7.5 YR 5/2, with MCC 7.5 YR 5/4, underbark.
Trunk Lenticels: (None visible)
Primary Branches:
Number per tree: About one set of 2-5 branches/whorl every 40 cm along trunk Length: Varies due to conical shape of tree; maximum of about 198 cm; minimum of about 30 cm. On average, branches grow about 20 cm to 30 cm, and then new branchlets form, radiating from the older, primary branch.
Diameter (at 4 years): About 30 mm to 35 mm
Surface texture: Somewhat scaly and rough
Pubescence: None.
Color:
   Mature: MCC 7.5 YR 5/4
   New Growth: MCC 5.0 YR 5/4
Branchlets:
Number per primary branch: About 3-4 every 15-20 cm along branch
Length: Maximum of about 60 cm; minimum of about 15 cm
Diameter: About 4 mm to 10 mm
Surface texture: Smooth to rough
Pubescence: None.
Color:
   Mature: MCC 7.5 YR 5/4
   New Growth: MCC 5.0 YR 5/4
Internode length: 4 to 6 growth cycles per year. Length varies by growth condition, averaging greater than 30 cm per cycle.
Internode diameter: Varies by position on the tree. Ranges from about 15 cm at base to 1.0 cm at top.
Branch lenticels: (None)
   Foliage:
   Juvenile Needles:
Arrangement: Single and aranged in spiral
Duration: Produced for about 3 months to 1 year.
Size:
   Length: About 20 mm to 40 mm
   Width: About 0.5 mm to 1.0 mm
Shape:
   Overall: Acicular
   Apex: Acute
   Base: Sessile
Margin: Entire
Orientation: Lateral
Aspect: Straight
Texture: Glabrous
Color:
   Upper surface: Fascicle base, MCC 7.5 GY 4/4, graduating to MCC 7.5 GY 4/4 at needle tip
   Under surface: Fascicle base, MCC 7.5 GY 4/4, graduating to MCC 7.5 GY 4/4 at needle tip
Scale leaves: None present
Mature Needles:
Arrangement: Evergreen needles, typically 3 needles per fascicle.
Duration: Without injury, needles can persist for about 2 years.
Size:
   Length (including sheath): About 120 mm to 220 mm
   Width: About 0.5 mm to 1.0 mm
Shape:
   Overall: Acicular
   Apex: Acute
   Base: Sessile
Margin: Entire
Orientation: Lateral
Aspect: Straight to somewhat twisted
Texture: Glabrous
Color:
   Upper surface: Fascicle base, MCC 7.5 GY 3/4 graduating to MCC 7.5 GY 3/4 at needle tip
   Under surface: Fascicle base, MCC 7.5 GY 3/4 graduating to MCC 7.5 GY 3/4 at needle tip
Venation:
Pattern: Linear
Color: MCC 7.5 GY 3/4
Sheath:
Size:
   Length: About 10 mm to 15 mm
   Width: About 2 mm to 3 mm
Color: MCC 7.5 YR 7/2
Fragrance: Similar to Turpentine and lemon-lime
Buds:
Type: Terminal and secondary
Shape: Narrowly ovoid
Length: About 5 mm to 15 mm
Width: About 3 mm to 6 mm
Texture: Covered with scales
Color: Apex, MCC 5 YR 6/4, and base, MCC 5 YR 6/4
Scales:
   Number: About 8 to 10
   Overall shape: Triangular
   Apex shape: Muncronate
   Base shape: Broadly rounded
   Color:
      Upper: MCC 2.5 YR 5/8
      Lower: MCC 2.5 YR 5/8
Cones:
Natural flowering season: February to March in Summerville, S.C.
Type: Monoecious; cone description provided for female cones.
   Immature Cone (Unopened):
   Overall Shape: Ovoid to cylindrical
   Length: About 75 mm to 130 mm
   Width: About 20 mm to 30 mm
   Weight: About 30 gm to 150 gm
   Texture: Irregular surface with short spine on each scale
   Color: Apex, MCC 2.5 YR 6/4, and base, MCC 2.5 YR 6/4
   Peduncle (rachis):
      Length: About 60 mm to 100 mm
      Width: About 3 mm to 6 mm
      Texture: Not visible in unopened cone, covered with scales
      Color: MCC 5 YR 4/8
   Scales:
      Number per peduncle (rachis): About 120
      Overall shape: Exposed portion (apex) loosely quadrilateral
      Apex shape: Loosely quadrilateral
      Base shape: Not visible in unopened cone
      Color: MCC 5 YR 5/4
Mature Cone (opened):
Age: Generally by about 10 years
Overall Shape Ovoid to narrowly conical
Length: About 75 mm to 150 mm
Width: About 40 mm to 60 mm
Weight: About 10 gm to 40 gm
Texture: Scale surfaces smooth except for short spine
Color: Apex, MCC 2.5 Y 8/4, and base, MCC 2.5 Y 8/4
Peduncle (rachis): Inseparable from scales that cover it
   Length: About 60 mm to 100 mm
   Width: About 3 mm to 6 mm
   Texture: Not visible, covered with scales Scales:
  Number per peduncle (rachis): About 120
  Type: Umbo-dorsal.
  Overall shape: Rectangular, flared at apex and narrowing at base
  Apex shape: Muncronate umbo
  Base shape: Narrowing to juncture with peduncle
  Color: MCC 2.5 Y 8/4
Seeds:
Number per scale: About 2
Type: Anemophilous
Overall Shape Somewhat triangular, with a raised center
Length: About 5 mm
Diameter: About 4 mm
Texture: Smooth
Color: Dark (MCC 5 YR 3/2) to light brown (MCC 7.5 YR 6/8), sometimes mottled
Seed wing:
  Attachment: Articulate
  Length: About 20 mm
  Width: About 8 mm
  Color: MCC 5 YR 4/6
Use: High Yield Industrial Plantations
DISEASE/PEST RESISTANCE: Free of fusiform rust infection in field trees through age 4. USDA Resistance Screening Center testing, using artificial inoculation with rust spores in two tests, yielded an average 22.2% infection where the resistant check had a 47.6% infection rate and the susceptible check had an 79.6% infection rate.
DISEASE/PEST SUSCEPTIBILITY: No further pest testing has been done.
WEATHER HARDINESS/TOLERANCE: No testing has been conducted Example 3

Genetic Fingerprinting Data of '96GE0034'

Molecular markers are widely used to assess genetic variation and relationships among and within a species (Faut, D., "Hypervariability of Simple Sequences as a General Source of Polymorphic DNA Markers," *Nucleic Acids Res.*, Vol. 17, 1989, pp. 6463-6471). Simple sequence repeat (SSR) markers have been useful for studying genetic relationships in loblolly pine (Liewlaksaneeyanawin, et al., "Single-copy, Species-transferable Microsatellite Markers Developed from Loblolly Pine ESTs," *Theor. Appl. Genet.*, Vol. 109, No. 2, 2004, pp. 361-369). Here, a set of 13 loblolly pine SSR markers were used to generate a unique DNA fingerprinting profile for loblolly pine genotype '96GE0034' (GE34). The SSR primer sequences used for this analysis and GenBank accession numbers are provided below.

Materials Methods

In order to generate microsatellite marker fingerprints for 12 different loblolly clonal varieties, NQ26, NQ90, ON10, PM212, PM229, GE34, PM51, PT1056, PT5992, NQ857, PT6615, and PT7207), 13 markers (Tables 3A and 3B) that were highly informative, easy and unambiguous to score, and well spaced across the genome were selected. Two of these markers, sifg-0493 and ript-1040 were from the same linkage, although they were still almost completely independent with a genetic map distance of 41 cM.

The 5' ends of all forward primers were modified with the universal m13 sequence CACGACGTTGTAAAACGAC (SEQ ID NO: 1), and the reverse primers all had the sequence GTTTCTT at the 5' end. These were used with a fluorescently labeled m13 primer of the same sequence as the 5' modification of the forward primers. Data was generated for one negative reagent control, the 12 CTAB extracted template DNA's, and three CTAB extracted DNA's of previously genotyped reference control samples of loblolly pine; B-145-L, 487NCS (=7-56), and 8-1070). The following reagents and concentrations were used in a 611 volume PCR reaction to amplify products: 20 ng template DNA, 5× colorless Gotaq™ rxn buffer with 15 mM $MgCl_2$ dilute to 1.0×, Promega dNTPs at 66 µM each base, 0.04 µM forward primer, 0.16 reverse primer, 0.16 µM fluorescently labeled M13 primer (dye label based on product pool in table), and 1 unit hot start Taq polymerase. Thermocycling was conducted in 96-well format using PTC-200 thermocyclers with heated bonnets from MJ-research using the following parameters: 94° C. for 2 minutes, followed by 20 cycles of 94° C. for 30 seconds, 65° C. minus 0.5° C. per cycle for 30 seconds, 72° C. for 1 minute, then 25 cycles of 92° C. for 30 seconds, 55° C. for 30 seconds, and 72° C. for 1 minute thirty seconds followed by a final extension at 72° C. for 15 minutes. The products were then held at 4° C. until analyzed.

PCR products were combined and diluted in 18 mega-ohm water into 4 product pools (Tables 3A and 3B) such that one template and several markers could be analyzed in the same capillary. Two micoliters of each product pool were then loaded on an ABI 3130 genetic analyzer using the default run module for a 36 cm capillary array modified by the addition of 5 minutes to the run time. An ABI LIZ600 internal size standard was used in each well at a concentration of 10 µl size standard/ml ABI HiDi formamide. Product fragments were then analyzed with GeneMapper™ 3.7 analysis software using microsatellite default settings as the analysis method.

Binning and naming of alleles were done using a scheme which allows for freedom of marker dye modification among projects to meet specific needs while still maintaining the same allele names for unifying data sets among projects. Allele names were first assigned to PCR products from each marker run with a 15-tree reference panel. Markers from these initial reference runs were labeled in one of four dye-labels, VIC, 6-FAM, NED, or PET. The allele names for a marker were based on fragment size as it appeared for whatever dye used in the reference sample runs. Any novel allele fragments in a subsequent project are named based on their relative base pair sizing within this reference frame, and subsequently become part of an additive set of named allele bins for that marker. The largest bin set for a marker is then used for all consecutive projects. Dye migration sizing differences among project runs are corrected when needed (i.e. marker A was run with 6-FAM in project 1, but VIC in project 2) for by shifting the positions of all bins in a set to the left (−) or right (+) based on dye migration difference values collected previously. Any further refinements needed due to slight run-to-run variation can also be judged by the binning of the reference controls and should be applied to all bins in a set equally. The three positive control reference samples included in PCR and sizing in this project matched previous allele calls.

SAS and Perl procs were used to process the data and GenAlEx v. 6.1 to calculate a genetic distance (methods=codom-genotypic) matrix.

TABLE 3A

Information on 13 microsatellite markers used for the DNA fingerprinting study.

| Locus name | Dye Label | Product Pools | Linkage Group | Position LG (cM) | Size range, bps | Number Reference Alleles |
|---|---|---|---|---|---|---|
| PtRIP-0619 | 6-FAM | 3 | 6 | 28.0 | 180-250 | 16 |
| PtRIP-1040 | VIC | 1 | 2 | 53.8 | 200-240 | 13 |
| PtRIP-1077 | VIC | 2 | 4 | 5.0 | 210-300 | 8 |
| PtSIFG-0193 | NED | 1 | 11 | 1.7 | 250-270 | 3 |
| PtSIFG-0493 | NED | 2 | 2 | 12.6 | 288-332 | 6 |
| PtSIFG-0566 | 6-FAM | 2 | 1 | 25.8 | 120-150 | 4 |
| PtSIFG-0737 | PET | 2 | 10 | 110.0 | 420-480 | 11 |
| PtSIFG-1190 | NED | 3 | 9 | 75.5 | 290-340 | 3 |
| PtSIFG-4222 | PET | 4 | 8 | 6.2 | 310-360 | 3 |
| PtSIFG-4233 | 6-FAM | 1 | 7 | 57.3 | 116-160 | 14 |
| PtSIFG-4304 | VIC | 3 | 12 | 37.0 | 408-424 | 7 |
| PtTX-4114 | 6-FAM | 4 | 3 | 35.0 | 110-170 | 9 |
| SsrPt-ctg9249 | PET | 1 | 5 | 19.9 | 170-200 | 3 |

TABLE 3B

GenBank accession numbers and sequences for SSR primer pairs used in genotyping analysis of line '96GE0034'

| Primer | Accession Number | Primer Sequence (5'-3') |
|---|---|---|
| PtRIP_0619 | BV683091 | CAGCTCTCTTAATAGCCTCGGGCACAT AGCAACGCTGAAGA (SEQ ID NO: 2) |
| PtRIP_1040 | BV683133 | TCAAGGAATTCATTGGAGCCTTTGGCC ATATCAAACCCAT (SEQ ID NO: 3) |
| PtRIP_1077 | BV683137 | AACATTCTAGCATGCCCCACTTGTGGT GGATGTCTCTCCTC (SEQ ID NO: 4) |
| PtSIFG_0193 | BV728742 | CCCATGCATCAATTCAAGTTTGTGCGT GGATATGGAAAAA (SEQ ID NO: 5) |
| PtSIFG_0493 | BV728661 | GAGAACATCTGCCTTGAGCCCTGGCAT GATGGGTTTCTCT (SEQ ID NO: 6) |
| PtSIFG_0566 | BV728755 | ACTTAGTGGGAAAGGGGGAATTCCTCA GCCAAAAGCTCTC (SEQ ID NO: 7) |
| PtSIFG_0737 | BV728669 | GCAAGGGGAATTGCTTATGAGGGATCG CATCAGCTGTAAT (SEQ ID NO: 8) |
| PtSIFG_1190 | BV728679 | CAGGTGGCTTGGATTTCATTTCATTCA AGCGTCCTGCTTA (SEQ ID NO: 9) |
| PtSIFG_4222 | BV728762 | CACCCTTTTCACGCAAGAATGCCTACG CATTATCCTTCCA (SEQ ID NO: 10) |
| PtSIFG_4233 | BV728685 | AGGGAAACCGCGGATTATAGCCGGAAT GAAGATTGCAGTT (SEQ ID NO: 11) |
| PtSIFG_4304 | BV728793 | CATGCATGTGTGGAGGAGTCTCATGTG CTTTGATCCCCT (SEQ ID NO: 12) |
| PtTX_4114 | BV728876 | ACACATGTCTTGAGGAGTTCAATTTGA TCTATAACTTTCACC (SEQ ID NO: 13) |
| SsrPt_ctg9249 | BV728813 | CTGCTCCCTCAGCTCTTCCAGACGTCA CTGCCATTACCC (SEQ ID NO: 14) |

Results and Discussion

All 13 markers gave excellent results for the 12 loblolly variety samples, plus our three control samples. Allelic peaks were easily binned and called using our existing marker panels and bin sets. Of the possible 13*12=156 data points (i.e., co-dominant genotypes), 155 were scored (<0.7% missing data).

All 12 variety samples provided distinct allelic profiles, with one pair of varieties (PT6615 and PT7207) showing high allele similarity.

The sample genotypes for all 13 markers and 12 varieties plus 3 control trees are provided in Tables 4A-4C. One missing data point is contained in the table for PM229 and is denoted by a 0 at each allele. '96GE0034' can be distinguished from other pine genotypes using as few as one primer set: PtTX4114 or PtSIFG_4304.

Tables 4A-4C.—Allele Fingerprinting Data from Twelve Loblolly Pine Genotypes Using Thirteen Primer Sets

TABLE 4A

| Genotype | PtRIP_1040 | | PtRIP_1077 | | PtSIFG_0193 | | PtSIFG_0493 | |
|---|---|---|---|---|---|---|---|---|
| GE34 | 217 | 217 | 247 | 247 | 256 | 258 | 314 | 317 |
| NQ26 | 223 | 223 | 235 | 245 | 256 | 258 | 308 | 314 |
| NQ857 | 217 | 227 | 241 | 243 | 253 | 256 | 314 | 317 |
| NQ90 | 217 | 217 | 235 | 247 | 253 | 258 | 314 | 314 |
| ON10 | 217 | 217 | 235 | 247 | 256 | 256 | 314 | 314 |
| PM212 | 217 | 217 | 241 | 247 | 256 | 258 | 308 | 317 |
| PM229 | 217 | 223 | 241 | 245 | 256 | 256 | 314 | 317 |
| PM51 | 217 | 217 | 247 | 247 | 256 | 258 | 308 | 317 |
| PT1056 | 217 | 217 | 247 | 257 | 256 | 256 | 314 | 314 |
| PT5992 | 217 | 217 | 241 | 245 | 256 | 256 | 317 | 317 |
| PT6615 | 217 | 227 | 241 | 245 | 256 | 256 | 317 | 317 |
| PT7207 | 217 | 227 | 241 | 245 | 256 | 258 | 317 | 317 |

TABLE 4B

| Genotype | PtSIFG_0566 | | PtSIFG_0737 | | PtSIFG_1190 | | PtSIFG_4222 | |
|---|---|---|---|---|---|---|---|---|
| GE34 | 129 | 135 | 444 | 456 | 312 | 312 | 344 | 346 |
| NQ26 | 129 | 135 | 444 | 444 | 312 | 312 | 344 | 344 |
| NQ857 | 135 | 135 | 450 | 462 | 312 | 312 | 342 | 344 |
| NQ90 | 129 | 135 | 444 | 444 | 309 | 312 | 344 | 344 |
| ON10 | 141 | 141 | 444 | 456 | 312 | 312 | 344 | 344 |
| PM212 | 135 | 141 | 444 | 450 | 312 | 312 | 344 | 346 |
| PM229 | 135 | 135 | 444 | 450 | 312 | 312 | 342 | 344 |
| PM51 | 135 | 141 | 444 | 450 | 312 | 312 | 344 | 346 |
| PT1056 | 129 | 141 | 444 | 444 | 312 | 312 | 344 | 344 |
| PT5992 | 129 | 135 | 444 | 450 | 303 | 312 | 342 | 344 |
| PT6615 | 129 | 135 | 444 | 456 | 303 | 312 | 342 | 344 |
| PT7207 | 129 | 135 | 444 | 456 | 303 | 312 | 342 | 344 |

TABLE 4C

| Genotype | PtSIFG_4233 | | PtSIFG_4304 | | PtTX4114 | | SsrPt_ctg9249 | | PtRIP_0619 | |
|---|---|---|---|---|---|---|---|---|---|---|
| GE34 | 124 | 136 | 418 | 420 | 130 | 136 | 175 | 178 | 221 | 221 |
| NQ26 | 122 | 124 | 420 | 420 | 136 | 140 | 175 | 178 | 221 | 221 |
| NQ857 | 122 | 136 | 420 | 420 | 138 | 140 | 175 | 175 | 221 | 225 |
| NQ90 | 122 | 122 | 416 | 420 | 132 | 140 | 178 | 184 | 221 | 221 |
| ON10 | 122 | 124 | 416 | 420 | 136 | 136 | 175 | 178 | 221 | 223 |
| PM212 | 122 | 122 | 416 | 420 | 138 | 140 | 175 | 178 | 221 | 223 |
| PM229 | 0 | 0 | 420 | 420 | 138 | 140 | 175 | 178 | 221 | 223 |
| PM51 | 122 | 136 | 416 | 420 | 136 | 140 | 175 | 178 | 223 | 223 |
| PT1056 | 122 | 124 | 416 | 420 | 136 | 140 | 175 | 178 | 221 | 221 |
| PT5992 | 122 | 122 | 420 | 420 | 138 | 144 | 175 | 178 | 223 | 223 |
| PT6615 | 124 | 136 | 420 | 420 | 134 | 136 | 175 | 178 | 221 | 221 |
| PT7207 | 122 | 124 | 420 | 420 | 134 | 136 | 175 | 178 | 221 | 221 |

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims. All publications and patent applications mentioned in this specification are indicative of the level of skill of those in the art to which the invention pertains.

All publications and patent applications are herein incorporated by reference to the same extent as if each individual publication or patent application were specifically and individually indicated to be incorporated by reference in its entirety.

What is claimed is:

1. A loblolly pine tree variety designated '96GE0034' (GE34), wherein a representative sample has been deposited under ATCC Accession No. PTA-9358.

2. A tissue culture of cells produced from the variety of claim 1.

3. Plant parts obtained from the loblolly pine tree of claim 1, wherein said parts have all of the morphological and physiological characteristics of the loblolly pine tree variety of claim 1.

4. Harvested products obtained from the loblolly pine tree of claim 1.

5. Wood produced from the harvested products obtained from the loblolly pine tree of claim 1.

6. A method of reproducing plants of the variety '96GE0034'), as deposited under ATCC Accession No. PTA-9358, comprising the step of multiplying '96GE0034' cells through somatic embryogenesis and reproducing '96GE0034' plants.

7. The method of claim 6, further comprising making root cuttings of the reproduced '96GE0034' plants and planting the root cuttings.

8. A method of producing loblolly pine progeny or a hybrid thereof, comprising the steps of (a) crossing loblolly pine '96GE0034', as deposited under ATCC Accession No. PTA-9358, either as the female or seed parent or male or pollen parent, with a second pine variety, and (b) selecting progeny.

9. The method according to claim 8, wherein the second pine variety is '96GE0034', as deposited under ATCC Accession No. PTA-9358.

10. A method of producing loblolly pine progeny or a hybrid thereof, comprising the steps of (a) crossing loblolly pine '96GE0034'), as deposited under ATCC Accession No. PTA-9358, as either the female or seed parent or male or pollen parent, with a second pine variety, (b) harvesting seeds produced from said cross, and (c) producing and selecting progeny from said harvested seeds.

11. The method according to claim 10, wherein the second pine variety is '96GE0034', as deposited under ATCC Accession No. PTA-9358.

12. A method of producing loblolly pine progeny, comprising the steps of (a) selfing loblolly pine '96GE0034', as deposited under ATCC Accession No. PTA-9358, and (b) selecting progeny.

13. Plant graft material obtained from the loblolly pine tree of claim 1, wherein said graft material has all of the morphological and physiological characteristics of the loblolly pine tree variety of claim 1.

* * * * *